United States Patent

Parry et al.

[11] 3,956,370
[45] May 11, 1976

[54] PREPARATION OF N-PHOSPHONOMETHYLGLYCINE

[75] Inventors: David Rees Parry, Wokingham; Clive Dudley Spencer Tomlin, Crowthorne, both of England

[73] Assignee: Imperial Chemical Industries Limited, London, England

[22] Filed: July 2, 1973

[21] Appl. No.: 375,912

[30] Foreign Application Priority Data
July 21, 1972   United Kingdom............... 34204/72

[52] U.S. Cl.......................... 260/502.5; 260/471 A; 260/473 R; 260/518 R; 260/521 R; 260/570.8 R; 260/570.9; 260/612 D; 260/646; 260/650 R
[51] Int. Cl.²......................................... C07F 9/38
[58] Field of Search................................ 260/502.5

[56] References Cited
UNITED STATES PATENTS

| | | | |
|---|---|---|---|
| 3,160,632 | 12/1964 | Toy et al............................ | 260/502.5 |
| 3,288,846 | 11/1966 | Irani et al........................ | 260/502.5 |
| 3,799,758 | 3/1974 | Franz................................ | 260/502.5 |

FOREIGN PATENTS OR APPLICATIONS

| | | | |
|---|---|---|---|
| 774,349 | 4/1972 | Belgium........................... | 260/502.5 |

OTHER PUBLICATIONS

Kosolspoff, "Organophosphorus Compounds" 1950, pp. 143, 148.
Vogel, "Practical Organic Chemistry", 3rd. Ed., 1957, pp. 122 to 133.
Van Wazer, "Phosphorus and its Compounds", Vol. 1 (1950), p. 379.

*Primary Examiner*—Joseph E. Evans
*Attorney, Agent, or Firm*—Cushman, Darby & Cushman

[57] ABSTRACT

A process of preparing the herbicide N-phosphonomethylglycine which comprises reacting an N-substituted glycine derivative of the formula:

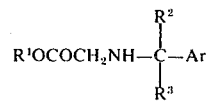

wherein $R^1$ is a hydrogen atom or an esterifying group, Ar is an aryl radical, and $R^2$ and $R^3$ each stand for a hydrogen atom or an aryl radical, with formaldehyde and phosphorous acid in an acidic aqueous medium to give an N-substituted N-phosphonomethylglycine derivative of the formula:

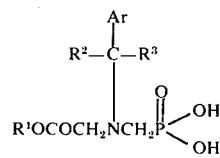

and thereafter reacting the said N-substituted N-phosphonomethylglycine with hydrobromic or hydriodic acid to remove the N-substituent, and recovering N-phosphonomethylglycine.

3 Claims, No Drawings

PREPARATION OF N-PHOSPHONOMETHYLGLYCINE

This invention relates to chemical processes, and in particular to a process for preparing the compound N-phosphonomethylglycine, having the formula:

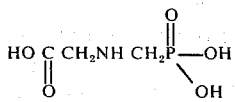

As disclosed in Belgian Pat. No. 774,349, N-phosphono-methylglycine is a broad spectrum herbicide having little or no residual effect. Various methods have been proposed for the preparation of N-phosphono-methylglycine. Example 14 of U.S. Pat. No. 3,160,632 for example, describes the oxidation of glycine-methylenephosphinic acid with mercuric chloride to form N-phosphonomethylglycine. In view of the problems of environmental pollution associated with the use of mercury compounds this method is obviously undesirable for large scale manufacturing use. Belgian Pat. No. 774,349 describes the preparation of N-phosphonomethylglycine from glycine and chloromethylphosphonic acid. The chlorine atom in chloromethylphosphonic acid is of low reactivity, however, and under the forcing conditions required to make the reaction take place byproducts are formed, for example by hydrolysis of the chloromethylphosphonic acid. Another byproduct is the compound formed by reaction of two moles of chloromethylphosphonic acid with one of the glycine, that is to say, the compound of structure $HOCOCH_2N[CH_2PO_3H]_2$ In principle, N-phosphonomethyl glycine could be obtained by reaction of one mole of gylcine with one mole each of formaldehyde and phosphorous acid. In practice, however, disubstitution of the glycine amino group tends to be the predominant reaction and the main product obtained is the compound of the structure $HOCOCH_2N[CH_2PO_3H]_2$ A method of preparing N-phosphonomethylglycine has now been devised which does not involve the use of toxic mercury compounds and in which the formation of byproducts is minimised.

According to the present invention, therefore, there is provided a process of preparing N-phosphonomethylglycine, which comprises reacting an N-substituted glycine derivative of the formula:

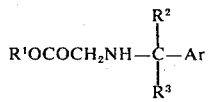

wherein $R^1$ is a hydrogen atom or an esterifying group, Ar is an aryl radical, and $R^2$ and $R^3$ each stand for a hydrogen atom or an aryl radical, with formaldehyde and phosphorous acid in an acidic aqueous medium to give an N-substituted N-phosphonomethyl glycine derivative of the formula:

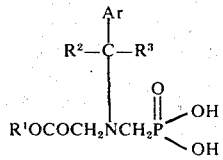

and thereafter reacting the said N-substituted N-phosphonomethylglycine derivative with hydrobromic or hydriodic acid to remove the N-substituent, and recovering N-phosphonomethylglycine.

The acidic aqueous medium in which the first stage of the process of the invention is carried out is preferably hydrochloric, hydrobromic, or hydriodic acid. The use of these acids is particularly convenient since they are volatile and can be removed by evaporation when it is required to isolate the N-substituted N-phosphonmethylglycine formed in the first stage of the process of the invention. Other acids, for example sulphuric acid or phosphoric acid, may be used in the acidic aqueous medium but are less convenient since they are not volatile, and it would be necessary to remove them chemically (for example by precipitating sulphuric acid as its barium salt) in order to isolate the glycine derivative. Oxidising acids, for example concentrated nitric acid, are not suitable for use in the acidic aqueous medium, since the formaldehyde used in the reaction would be destroyed by oxidation. The condensation of formaldehyde with phosphorus acid and the N-substituted glycine is preferably carried out at a temperature of at least 100° C. Lower temperatures may be used, but will result in a slower rate of reaction. It is preferred to carry out the reaction at the temperature of the acidic aqueous medium when heated under reflux. This temperature will vary depending upon the particular acid used and upon its concentration, but will be in the region from 100° to 130° C. Higher temperatures, for example, up to 150° C or more, can be achieved by heating the reaction mixture under pressure, and will give shorter reaction times.

In the second stage of the process of the invention, in which the N-substituted N-phosphonomethylglycine derivative is reacted with hydrobromic or hydriodic acid to remove the N-substituent and in which N-phosphonomethylglycine is recovered, the hydrobromic acid used is preferably concentrated, containing 46 to 48% of hydrogen bromide, and having a density of about 1.48 grams per ml. at 20° C. The hydriodic acid is also preferably concentrated, containing about 55% of hydrogen iodide and having a density of about 1.65 to 1.7 grams per ml at 20° C. Less concentrated acids may be used if desired, but a reduced speed of reaction is then to be expected. The reaction is preferably carried out at the temperature of the acid when heated under reflux, which is about 126° C in the case of concentrated hydrobromic acid and about 127° C in the case of concentrated hydriodic acid. Lower temperatures (for example down to 100° C) can be used but will result in increased time taken for the reaction to be completed. Higher temperatures (for example up to 150°C) may be used but in this case the reaction must be carried out under pressure, which is less convenient.

In the reaction with hydrobromic or hydriodic acid, the bond between the nitrogen atom of the N-substituted N-phosphonomethylglycine and the group

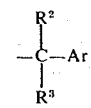

is broken with the formation of N-phosphonomethylglycine and a product

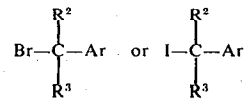

The latter bromo or iodo compound is readily separated from the aqueous solution of N-phosphonomethylglycine by conventional methods well known in the art, for example by extraction with a water immiscible solvent such as petroleum ether. The N-phosphonomethylglycine may then be isolated for example by evaporating the aqueous solution in a vacuum.

A particularly convenient way of performing the process of the invention comprises carrying out the condensation of formaldehyde and phosphorous acid with the N-substituted glycine derivative in aqueous hydrobromic or hydriodic acid, the N-substituted N-phosphonomethylglycine derivative so obtained then being heated to reflux, without being isolated, in the same reaction medium in which it was formed, to bring about the removal of the N-substituent and the formation of the N-phosphonomethylglycine, which is then isolated by conventional methods. Thus, by using hydrobromic acid or hydriodic acid as the aqueous acid medium for the condensation of formaldehyde and phosphorous acid with the N-substituted glycine derivative, the isolation of the intermediate N-substituted N-phosphonomethylglycine is avoided and the whole process can be carried out in one vessel.

When the group $R^1$ in the N-substituted glycine derivative of formula:

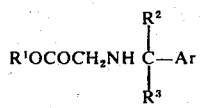

is an esterifying group, it is usually replaced by a hydrogen atom in the first stage of the process of the invention, that is to say during the condensation with formaldehyde and phosphorous acid, since the acidic aqueous medium employed for the reaction tends to bring about hydrolysis of the ester linkage.

The esterifying group $R^1$ in the foregoing formula may be, for example, a hydrocarbyl group of from 1 to 20 atoms, for example an alkyl group of from 1 to 6 carbon atoms. The aryl group Ar is preferably a phenyl group. The phenyl group may, if desired, bear one or more substituents which do not interfere with the reactions involved in the process of the invention, but there appears to be no particular advantage to be gained thereby. Examples of substituents which may be used include alkyl, alkoxy, and nitro groups.

Preferred alkyl and alkoxy groups are those of 1 to 6 carbon atoms. When the groups $R^2$ and $R^3$ are aryl radicals they are preferably phenyl groups, which may be optionally substituted for example, by one or more alkyl, alkoxy, or nitro groups.

Conveniently the aryl group Ar in the N-substituted glycine derivative of formula

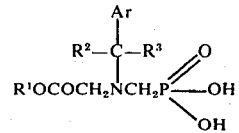

is an unsubstituted phenyl radical, and the groups $R^2$ and $R^3$ are hydrogen atoms.

The N-substituted glycine derivatives of formula:

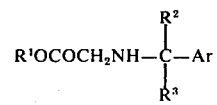

used as starting materials for the process of the invention may be prepared by known methods, for example by the process outlined in Scheme A or Scheme B below.

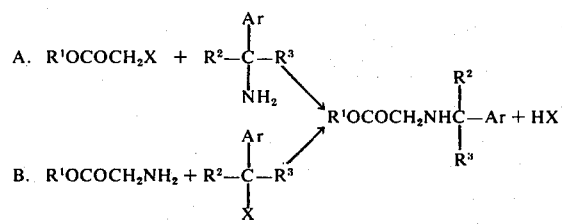

In the above reaction schemes, X represents a chlorine, bromine, or iodine atom, while the remaining symbols have the meanings previously assigned to them.

It may be noted that the bromo- derivative

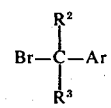

or the iodo derivative

formed in the last stage of the process of the invention may be converted into the corresponding amino compound

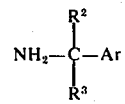

by reaction with ammonia, and the latter then converted into the starting material for the process of the invention by reaction with a halogenoacetic acid derivative according to Scheme A above. The N-substituent may therefore be recycled and used in a further preparation of N-phosphonomethylglycine.

N-phosphonomethylglycine prepared according to the process of the invention may readily be converted into its salts and esters by methods well known to those skilled in the art. Thus salts may be obtained by partial or complete neutralisation of N-phosphonomethylglycine with bases such as alkali metal hydroxides, ammonia, or organic amines. Esters may be obtained by reaction of N-phosphonomethylglycine with an alcohol in presence of an acid catalyst such as hydrogen chloride.

As a result of the experimental work involved in devising the process of the invention, it has been discovered that N-phosphonomethylglycine may be obtained by recrystallisation from water in a novel form having a melting point of 314° C with decomposition, as compared with the previously known form of N-phosphonomethylglycine having a melting point of 230° with decomposition, which is obtained by precipitating N-phosphonomethylglycine from solution by adding hydrochloric acid. The novel form of N-phosphonomethyl glycine has been found to be less soluble in water than the previously known form. Recrystallisation from water may be preferable to precipitation with hydrochloric acid, in that the latter method could involve problems with disposal of waste when operating on a large scale.

By way of illustration of the preparation of N-substituted glycine derivatives of formula:

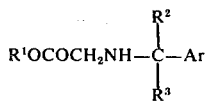

used as starting materials for the process of the invention, the following description of the preparation of N-benzyl ethyl glycinate is given. Benzylamine (214 g; 2 M) and ethyl chloracetate (122 g, 1 M) were stirred in toluene solution (1 liter) for 5 hours at 95°C. The white precipitate of benzylamine hydrochloride was filtered off, and the toluene removed under reduced pressure to leave a mixture of oily liquid and further benzylamine hydrochloride. The benzylamine hydrochloride was filtered off and the pale yellow oil distilled under high vacuum to give N-benzyl ethyl glycinate (121 grams 63%) of boiling point 97 to 102°/0.1 mm. The infra red spectrum of this material was identical with that of an authentic sample of N-benzyl ethyl glycinate.

The invention is illustrated by the following Examples.

EXAMPLE 1

This Example illustrates the preparation of N-benzyl-N-phosphonomethylglycine, having the formula:

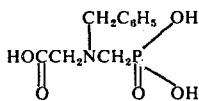

N-Benzyl ethyl glycinate (120 g. 0.622 M) prepared as set forth in the foregoing description, was dissolved in a mixture of dionised water (400 ml.) and concentrated hydrochloric acid (140 ml.) A solution of phosphorous acid (51.0 g. 0.622 M) in deionised water (100 ml.) was added, and the solution heated to reflux. Formalin solution (40% w/w formaldehyde solution in water 131 ml) was aded over 30 minutes, giving a light pink solution. After heating for 1 hour under reflux, paraformaldehyde (30.8 g) was added in portions over 10 minutes and the solution heated under reflux for a further 4 hours, slowly turning yellow in colour. The solution was evaporated to dryness under reduced pressure and finally dried at 0.1 millimeters pressure over phosphorus pentoxide. The semi-solid waxy product slowly crystallised over a period of several weeks, the product then having a melting point of about 35°C. The yield of dry material was 155 grams.

EXAMPLE 2

This Example illustrates the preparation of N-phosphonomethylglycine by debenzylation of N-benzyl N-phosphonomethyl glycine.

N-Benzyl-N-phosphonomethylglycine (65 g.) prepared by the method of Example 1 was dissolved in aqueous hydrobromic acid (46 – 48% w/w, 400 ml.) and the pale yellow solution heated under reflux for 16 hours. The oily layer of benzyl bromide which separated was extracted with petroleum ether (b.p. 60°–80°, 200 ml.) and the pale yellow hydrobromic acid solution evaporated to dryness under reduced pressure. The light brown crystalline product was dissolved in ethanol (300 ml.) and the solution quickly filtered and allowed to stand at room temperature. After a few minutes a white solid began to separate. After cooling at 0°C for 3 hours, the solid (approximately 20 g. m.p. 222°C decomp.) was collected and recrystallised from water to yield N-phosphonomethylglycine (17.2 g 41%) This material became coloured and softened at 230° – 235°C but did not decompose until 314°C. This material was analysed. Found: C, 21.13; H 4.52; N 8.49% Calculated for $C_3H_8NO_5P$: C, 21.31; H, 4.77; N, 8.28% The melting point of analytically pure N-phosphonomethyglycine, purified by slow precipitation from strongly acid aqueous solution, has been reported in Belgian Pat. No. 774,349 to be 230°C (decomp.) A sample of N-phosphonomethylglycine was purified by precipitation from strongly acid (HCl) aqueous solution and was found to have a melting point of 230° (decomp.) This material was found to have nuclear magnetic resonance spectrum identical with that of the material recrystallised from water and having a melting point of 314° (decomp.) The solvent used for studying the nuclear magnetic resonance spectrum was deuterium oxide. The infra-red spectra of Nujol mulls of the two materials (m.p. 230° and m.p. 314°) were examined and found to be very similar with some minor differences in peak heights. The solubility of the two forms in water was determined at various temperatures by adding the finely powdered solids to deionised water until saturated. The results are given below.

| Temperature °C | Weight dissolved in 50 ml. water (in grams) | |
|---|---|---|
| | 314°C form | 230°C form |
| 23 | 1.1 | 1.0 |
| 30 | 1.2 | 1.1 |
| 40 | 1.3 | 1.3 |
| 50 | 1.6 | 1.7 |
| 60 | 1.8 | 2.2 |
| 70 | 2.2 | 3.1 |
| 80 | 2.9 | 4.1 |
| 90 | 4.1 | 5.3 |
| 100 | 4.3 | 6.8 |

We claim:
1. A process of preparing N-phosphonomethyl-glycine having the formula:

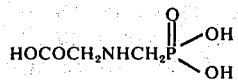

which comprises reacting an N-substituted glycine derivative of the formula:

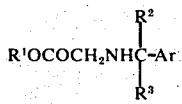

wherein $R^1$ is a hydrogen atom or an esterifying group, Ar is an aryl radical, and $R^2$ and $R^3$ are each selected from the group consisting of hydrogen atoms and aryl radicals, with formaldehyde and phosphorous acid in a nonoxidizing acidic aqueous medium to give an N-substituted-N-phosphonomethylglycine derivative of the formula:

and thereafter reacting the said N-substituted-N-phosphonomethylglycine with an acid selected from the group consisting of hydrobromic and hydriodic acids, and recovering N-phosphono-methylglycine.

2. A process according to claim 1 wherein the nonoxidizing acidic aqueous medium comprises hydrochloric, hydrobromic, or hydriodic acid.

3. A process according to claim 1, wherein the condensation of the N-substituted glycine derivative with formaldehyde and phosphorous acid is carried out at a temperature in the range from 100°C to 150°C.

* * * * *